United States Patent
Anderson et al.

(10) Patent No.: US 12,312,306 B2
(45) Date of Patent: May 27, 2025

(54) DEGRADATION OF PLASTIC MATERIALS INTO TEREPHTHALIC ACID (TPA), ETHYLENE GLYCOL AND/OR OTHER MONOMERS THAT FORM THE PLASTIC MATERIALS

(71) Applicant: ECOLE POLYTECHNIQUE FEDERALE DE LAUSANNE (EPFL), Lausanne (CH)

(72) Inventors: Samantha Lynn Anderson, Pully (CH); Christopher Patrick Ireland, Pont-de-la-Morge (CH); Berend Smit, St-Sulpice (CH); Kyriakos Stylianou, Sion (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 797 days.

(21) Appl. No.: 17/433,137

(22) PCT Filed: Feb. 25, 2020

(86) PCT No.: PCT/EP2020/054942
§ 371 (c)(1),
(2) Date: Aug. 23, 2021

(87) PCT Pub. No.: WO2020/173961
PCT Pub. Date: Sep. 3, 2020

(65) Prior Publication Data
US 2022/0153674 A1    May 19, 2022

(30) Foreign Application Priority Data
Feb. 27, 2019 (EP) .................................... 19159827

(51) Int. Cl.
C07C 29/09 (2006.01)
C07C 51/09 (2006.01)
C08J 11/14 (2006.01)

(52) U.S. Cl.
CPC ............ *C07C 51/09* (2013.01); *C07C 29/095* (2013.01); *C08J 11/14* (2013.01); *C08J 2367/02* (2013.01)

(58) Field of Classification Search
CPC ...................................................... C07C 51/09
See application file for complete search history.

(56) References Cited

U.S. PATENT DOCUMENTS

| | | | |
|---|---|---|---|
| 5,254,666 A | 10/1993 | Benzaria | |
| 7,897,651 B2 * | 3/2011 | Ikenaga | C08J 11/24 522/182 |
| 9,550,713 B1 * | 1/2017 | Essaddam | C07C 29/1285 |
| 2010/0133088 A1 * | 6/2010 | Hajek | C08J 11/24 204/157.87 |
| 2011/0162955 A1 * | 7/2011 | Butzloff | B01J 23/30 977/734 |
| 2022/0153674 A1 | 5/2022 | Anderson et al. | |

FOREIGN PATENT DOCUMENTS

| | | |
|---|---|---|
| CN | 101066904 A | 11/2007 |
| EP | 3931172 A1 | 1/2022 |
| WO | 2009033129 A1 | 3/2009 |

OTHER PUBLICATIONS

Buzarovska et al, Journal of Applied Polymer Science, v. 114, 3118-3124, 2009 (Year: 2009).*
Miyauchi et al, Environ. Sci. Technol. 2008, 42, 4551-4554 (Year: 2008).*
Examination Search Report from Canadian Application No. 3,130,569 dated Dec. 1, 2023.
Written Opinion from corresponding PCT application No. PCT/EP2020/054942 dated May 12, 2020.
International Search Report from corresponding PCT application No. PCT/EP2020/054942 dated May 12, 2020.

* cited by examiner

*Primary Examiner* — Irina Krylova
(74) *Attorney, Agent, or Firm* — Harness Dickey & Pierce P.L.C.

(57) ABSTRACT

The invention relates to a method for degradation of plastic materials into terephthalic acid (TPA) and/or ethylene glycol and/or other monomers that form the plastic materials.

9 Claims, 8 Drawing Sheets

DEGRADATION OF PLASTIC MATERIALS INTO TEREPHTHALIC ACID (TPA), ETHYLENE GLYCOL AND/OR OTHER MONOMERS THAT FORM THE PLASTIC MATERIALS

FIELD OF THE INVENTION

The invention relates to a method for degradation of plastic materials into terephthalic acid (TPA) and/or ethylene glycol and/or other monomers that form the plastic materials.

BACKGROUND OF THE INVENTION

Poly(ethylene terephthalate), widely known as PET, is a semicrystalline thermoplastic polyester that is used in a variety of industries in the form as fibers, sheets, films, and bottles. Its stability, high mechanical strength, high resistance to atmospheric and biological agents, and good aesthetic appearance has led to its prevalence in both the commercial and industrial sectors. Recently, it has been reported that the world consumption of PET is approximately 20 million tons per year, with its estimated forecast to exceed that by 2021 due to an annual increase of 3.6%. While PET has become an inextricable part of our lives, environmental concerns have been raised about its pollution in our ocean and landfills. As of 2015, it has been estimated that only 9% of plastic has been recycled, 12% incinerated, and 79% has accumulated in our landfills or the natural environment. Furthermore, microplastic contamination in the environment, and subsequently in marine invertebrates and other mammals has also recently emerged as a serious problem due to the adverse effects associated with their ingestion such as effects on reproduction, decreased neurofunctional activity, morality, and more.

The environmental effects of PET production is not only limited to post-consumer PET contaminating the landfills. It has also been reported that while other industrial sectors can lower their carbon footprint, the petrochemical industry which produces PET will ultimately increase their greenhouse gas emissions with increased PET production, thereby eroding climate benefits. The most common industrial synthesis route of PET is through the polycondensation of ethylene glycol (EG) and dimethyl terephthalate (DMT) or purified terephthalic acid (TPA) using a continuous melt-phase polymerization process with temperatures of approximately 280° C. The base chemicals for this process (EG, DMT, and TPA) are typical bulk chemicals that the petrochemical industry obtains from catalytic reforming of petroleum naptha to paraxylene. Therefore, closing the recycling loop has a cascading effect from removing post-consumer waste from our environment to lowering greenhouse gas emission by increasing the supply of TPA within the market, and decreasing our reliance of TPA from the petroleum industry.

Following the consumption of PET, either commercially or industrially, users typically recycle the product(s) via four distinct methods, which are referred to as primary through quaternary recycling depending on the quality of the recycled product. While primary recycling exclusively deal with industrial PET scrap and salvage, secondary recycling physically reprocesses consumer PET through grinding, washing, drying and reprocessing. However, the quality of PET obtained through secondary recycling is not virgin, and therefore much of it ends up being incinerated to recovery the energy content (quaternary recycling). Ultimately, tertiary recycling, or the depolymerization of PET to its starting monomers is the ideal method to close the recycling loop, as the monomers can be resold back to the chemical industry to form virgin PET, or other products.

Tertiary recycling, that is, the chemical conversion of PET into useful base products can be done through solvolysis, which is divided into i. hydrolysis, ii. aminolysis, iii. ammonolysis, iv. methanolysis, and v. glycolysis. Industrially, hydrolysis is an ideal process as the components generated, TPA and EG, are the original components used to make PET. However, the main disadvantage is that current methods use high temperatures (200-350° C.) and pressures (>1.1 MPa). Neutral hydrolysis of PET at room temperature has been reported to be hardly perceivable by generic analytical methods as it's completely insoluble in solvents such as water and ethanol. However, if these solvents are combined with an acid or a base, depolymerization can begin given enough time. The mechanism for either acidic/neutral or alkaline hydrolysis of PET involves the breakage of ester linkages in the main chain via $H^+$ or $OH^-$, creating one carboxyl and one hydroxyl end group (TPA and EG). Alkaline hydrolysis of PET is commonly carried out in a NaOH or KOH solution (4-20 wt %), with the best results using a PET:NaOH weight ratio of 1:20 at about 100° C. in 2 hrs.

The other methods, such as aminolysis/ammonolysis, methanolysis, and glycolysis all typically yield products other than TPA such as bis (2-hydroxyethylene) terephthalamide, DMT, and bis (2-hydroxyethyl) terephthalate, respectively. While each method has its own unique advantage, the drawback associated with them is the use of high pressures and/or temperatures, exotic/expensive catalysts, the conversion of the associated products to TPA, as well as high costs to separate and refine the product. While the chemical degradation or depolymerization of PET has come a long way since the 1950s it is far from complete, and for each process research has shown how to overcome problems relating to long reaction times, low yields, harsh conditions, and pollution. The caveat is that while these processes have all been described to successfully recycle PET, no one specific method solves all these problems simultaneously.

Therefore, there exists a need for an effective, inexpensive, robust and practical technology for degrading plastic waste, such as PET material, and simultaneously producing terephthalic acid (TPA), and/or ethylene glycol (EG) and/or other monomers that form the one or more plastic material.

SUMMARY OF THE INVENTION

An aspect of the present invention provides a method of alkaline hydrolysis of one or more plastic polymers into terephthalic acid (TPA) and/or ethylene glycol (EG) and/or other monomers that form the one or more plastic polymers, the method comprising
  a) contacting the one or more plastic polymers with a metal oxide in a solution in the presence of a base to provide a reaction mixture;
  b) stirring the reaction mixture during appropriate time under UV light;
  c) recovering terephthalic acid, ethylene glycol and/or the other monomers from the reaction mixture.

DETAILED DESCRIPTION OF THE INVENTION

Figure 1:
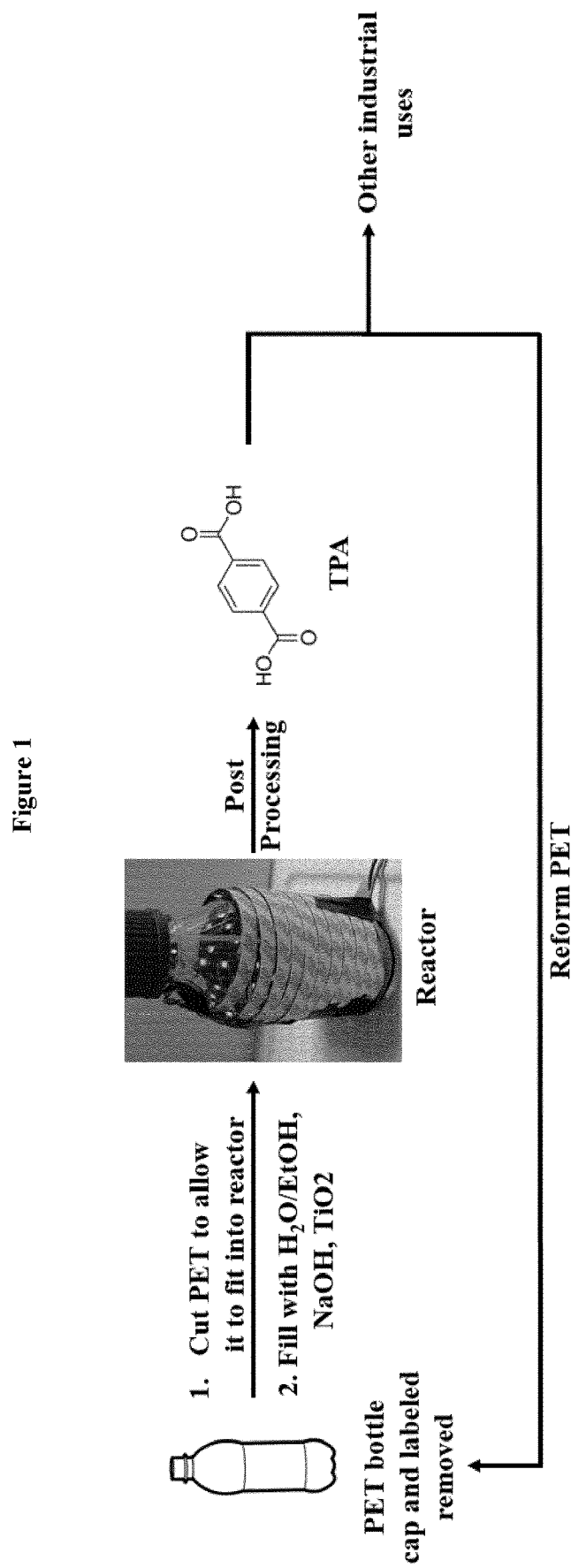
FIG. 1 shows recycling set up developed for the room temperature depolymerization of plastic polymers, such as PET, using radicals.

All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components. In addition, as used in the specification and claims, the language "comprising" can include analogous embodiments described in terms of "consisting of" and/or "consisting essentially of".

As used in the specification and claims, the term "and/or" used in a phrase such as "A and/or B" herein is intended to include "A and B", "A or B", "A", and "B".

As used in the specification and claims, the singular forms "a", "an" and "the" include plural references unless the context clearly dictates otherwise.

As used in the specification and claims, the term "monomers" used in "other monomers that form the one or more plastic polymers" refers to the monomers that are linked together to form the plastic polymer chain. Polymers, both natural and synthetic, are created via polymerization of monomers.

The inventors have developed a method that allows recycling plastic polymers, such as poly(ethylene terephthalate) (PET), at room temperature, using radicals to enhance the rate of alkaline hydrolysis in a short period of time. Despite the low temperature and short reaction times, quantitative yields of terephthalic acid (TPA) and/or ethylene glycol (EG) and/or other monomers that form the one or more plastic polymers can be achieved. Enhancing the degradation process was achieved through the use of UV lights, such as UV black lights, and the addition of a metal oxide, such as TiO$_2$. TiO$_2$ is commercially available, and is extensively used as a photocatalyst for the photocatalytic degradation of pollutants, and as a semiconductor. Since the method of the present invention is operated at room temperature, the energy penalty of recycling plastic polymers, such as PET, into its main components is significantly reduced. Furthermore, due to the nature of the setup, the method of the present invention allows for an easy separation of terephthalic acid (TPA) from ethylene glycol (EG) or other monomers, and other salts present at the end of the reaction.

Typically, the method of the present invention is a radically enhanced alkaline hydrolysis which can degrade plastic polymers, such as PET, containers and/or fibers without prior treatment (i.e washing or grinding), in about 4 hours, with high yields of TPA (>99%) and at room temperature and atmospheric pressure. The reaction relies on a UV light, such as UV black light, reactor using a metal oxide, such as TiO$_2$, to supply increase the rate of hydrolysis by the addition of radicals, resulting in the depolymerization of various post-consumer waste plastic polymers, such as PET, containers.

Thus an aspect of the present invention provides a method of alkaline hydrolysis of one or more plastic polymers into terephthalic acid (TPA) and/or ethylene glycol (EG) and/or other monomers that form the one or more plastic polymers, the method comprising
  a) contacting the one or more plastic polymers with a metal oxide in a solution in the presence of a base to provide a reaction mixture;
  b) stirring the reaction mixture during appropriate time under UV light; preferably at least 1 minute;
  c) recovering terephthalic acid, ethylene glycol and/or the other monomers from the reaction mixture.

An embodiment of the present invention provides a method of alkaline hydrolysis of one or more plastic polymers into terephthalic acid (TPA) and/or ethylene glycol (EG), the method comprising
  a) contacting the one or more plastic polymers with a metal oxide in a solution in the presence of a base to provide a reaction mixture;
  b) stirring the reaction mixture during appropriate time, preferably at least 1 minute or during 30 minutes to 72 hours, more preferably during 2 to 72 hours under UV light;
  c) recovering terephthalic acid and/or ethylene glycol from the reaction mixture.

An embodiment of the present invention provides a method of alkaline hydrolysis of one or more plastic polymers into terephthalic acid (TPA), the method comprising
  a) contacting the one or more plastic polymers with a metal oxide in a solution in the presence of a base to provide a reaction mixture;
  b) stirring the reaction mixture during appropriate time, preferably at least 1 minute, more preferably 30 minutes to 72 hours or 2 to 72 hours under UV light;
  c) recovering terephthalic acid from the reaction mixture.

In some embodiments of the method of the present invention, the one or more plastic polymers is selected from the group comprising poly lactic acid (PLA), polyethylene terephthalate (PET), polybutylene terephthalate (PBT), polytrimethylene terephthalate (PTT), polyethylene isosorbide terephthalate (PEIT), polyethylene furanoate (PEF), polyvinyl chloride (PVC), polyvinylidene chloride (PVDC) or combinations thereof. In some other embodiments of the method of the present invention, the one or more plastic polymers is selected from the group comprising poly lactic acid (PLA), polyethylene terephthalate (PET), polybutylene terephthalate (PBT), polytrimethylene terephthalate (PTT), polyethylene isosorbide terephthalate (PEIT), polyethylene furanoate (PEF), or combinations thereof. In some other embodiments of the method of the present invention, the one or more plastic polymers is selected from the group comprising poly lactic acid (PLA), polyethylene terephthalate (PET), polybutylene terephthalate (PBT), polytrimethylene terephthalate (PTT), polyethylene isosorbide terephthalate (PEIT) or combinations thereof. Most preferably, the one or more plastic polymers is polyethylene terephthalate (PET).

In some embodiments of the method of the present invention, the other monomers that form the one or more plastic polymers are selected from the group comprising lactic acid, butylene glycol, 1,3-propylene, furandicarboxylic acid, vinyl chloride, 1,1-dicholorethane, propylene, styrene, ethylene, acrylonitrile, polybutadiene. In some other embodiments of the method of the present invention, the other monomers that form the one or more plastic polymers are selected from the group comprising lactic acid, butylene glycol, 1,3-propylene, furandicarboxylic acid. In some other embodiments of the method of the present invention, the other monomers that form the one or more plastic polymers are selected from the group comprising lactic acid, butylene glycol, 1,3-propylene.

In some embodiments of the method of the present invention, the metal oxide is selected from the group comprising $TiO_2$, $V_2O_5$, $Cr_2O_3$, $CrO_3$, $Mn_2O_3$, FeO, $Fe_2O_3$, $Fe_3O_4$, $Co_2O_3$, NiO, CuO, $Cu_2O$, ZnO, $ZrO_2$, $Nb_2O_5$, $Mo_2O_3$, RuO, $RuO_2$, $RuO_4$, $RhO_2$, $Rh_2O_3$, PdO, $Ag_2O$, $Ag_2O_2$, CdO, $In_2O_3$, $Al_2O_3$, $La_2O_3$, $CeO_2$, $Ce_2O_3$, $HfO_2$, $Ta_2O_5$, $WO_3$, $ReO_2$, $ReO_3$, $Re_2O_3$, $OsO_2$, $OsO_4$, $IrO_2$, $PtO_2$, $Au_2O_3$, $Li_2O$, $Na_2O$, $K_2O$, MgO, CaO, SrO, BaO, or combinations thereof. Preferably the metal oxide is $TiO_2$ or P25. In some embodiments of the method of the present invention, the metal oxides disclosed above or combinations thereof are used alone. In some other embodiments of the method of the present invention, the metal oxides disclosed above or combinations thereof are bound to a surface selected from the group comprising $TiO_2$, P25, or any other physical or chemical mix of metal oxides disclosed above. In some further embodiments of the method of the present invention, the metal oxide or combinations of the metal oxides chemically or physically mixed from the group disclosed above are bound on their surface to a metal selected from the group comprising Pt, Rh, Pd, Ag, Au, Zn, Ni, Ir.

In some preferred embodiments of the method of the present invention, the metal oxide is selected from the group comprising $TiO_2$, ZnO, $ZrO_2$, $Nb_2O_5$, $Ta_2O_5$, RuO, $Fe_2O_3$, WO. The most preferably, the metal oxide is $TiO_2$.

The role of P25, or $TiO_2$, or metal oxides, or alternatively P25, or $TiO_2$, or metal oxides bound to a surface, such as P25, is to interact with the UV black light, and produce radicals from this interaction, which increase the rate of the reaction.

In some embodiments of the method of the present invention, the solution is a solution containing an alcohol and/or water, or the solution is an aqueous alcoholic solution. Alcohol and water can be present at different ratios, such as alcohol:water from 100:0 to 0:100, or 90:10 to 10:90, or 80:20 to 20:80, or 50:50 to 90:10, preferably 50:50 or 80:20. The alcohol comprises 1 to 5 carbon atoms and/or the alcohol is selected from the group comprising methanol, ethanol, propanol, butanol, pentanol or combinations thereof. Preferably, the alcohol is ethanol. More preferably the aqueous alcoholic solution is 80:20 ethanol:water solution. Most preferably the solution is ethanol or 90:10 to 10:90 ethanol:water solution.

In some embodiments of the method of the present invention, the water is selected from the group comprising deinoized water, wastewater, seasalt water, tap water, river water, lake water. Most preferably the water is deinoized water.

In some embodiments of the method of the present invention, the base is selected from the group comprising NaOH, NaOMe, NaOEt, NaO$^i$Pr NaO$^t$Bu, KOH, KOMe, KOEt, KO$^i$Pr KO$^t$Bu, LiOH, LiOMe, LiOEt, LiO$^i$Pr, LiO$^t$Bu, Rb(OH), RbOMe, RbOEt, RbO$^i$Pr, RbO$^t$Bu CsOH, CeOMe, CsOEt, CsO$^i$Pr, CsO$^t$Bu, Fr(OH), FrOMe, FrOEt, FrO$^i$Pr, FrO$^t$Bu, Be(OH)$_2$, Be(OMe)$_2$, Be(OEt)$_2$, Be(O$^i$Pr)$_2$, Be(O$^t$Bu)$_2$, Mg(OH)$_2$, Mg(OMe)$_2$, Mg(OEt)$_2$, Mg(O$^i$Pr)$_2$, Mg($^t$OBu)$_2$, Ca(OH)$_2$, Ca(OMe)$_2$, Ca(OEt)$_2$, Ca(O$^i$Pr)$_2$, Ca($^t$OBu)$_2$, Sr(OH)$_2$, Sr(OMe)$_2$, Sr(OEt)$_2$, Sr(O$^i$Pr)$_2$, Sr($^t$OBu)$_2$, Ba(OH)$_2$, Ba(OMe)$_2$, Ba(OEt)$_2$, Ba(O$^i$Pr)$_2$, Ba($^t$OBu)$_2$, Ra(OH)$_2$, Ra(OMe)$_2$, Ra(OEt)$_2$, Ra(O$^i$Pr)$_2$, Ra($^t$OBu)$_2$, NH$_4$(OH), or combinations thereof.

In some embodiments of the method of the present invention, the base is selected from the group comprising NaOH, NaO$^t$Bu, KOH. The most preferably the base is NaOH.

In some embodiments of the method of the present invention, the alkaline hydrolises is carried out at pH 7 to 14, or 8 to 13, or 9 to 12, or 7 to 12, or 7 to 10, or 7 to 9, or 8 to 14, or 8 to 12, or 8 to 10, or 9 to 14, or 9 to 12, or 9 to 10.

In some embodiments of the method of the present invention, the ratio plastic polymer:base is from 1:1 to 1:20 or 1:1 to 1:10. In preferred embodiments, the ratio plastic polymer:base is 1:20, 1:7.5, 1:1 or 1:3. In other preferred embodiments, the ration plastic polymer:base is 2:1 to 3:1, preferably 2:1 or 3:1.

In some embodiments of the method of the present invention, the ratio plastic polymer:metal oxide is from 1:0.0375 to 1:0.00125. In preferred embodiments, the ratio plastic polymer:metal oxide is 1:0.0375, 1:0.015, 1:0.0075, or 1:0.00125.

In some embodiments of the method of the present invention, the appropriate time in stirring step is at least 30 minutes, 1, 2, 4, 6, 8, 10, 12, 14, 15, 16 or 18 hours. In some other embodiments of the method of the present invention, the appropriate time in stirring step is at least 1 minute. In some other embodiments of the method of the present invention, the appropriate time in stirring step is 1 minute to 1 month. In some other embodiments of the method of the present invention, the appropriate time in stirring step is selected from the group comprising 30 minutes to 72 hours, 30 minutes to 48 hours, 30 minutes to 24 hours, 1 to 72 hours, 1 to 48 hours, 1 to 24 hours, 2 to 72 hours, 2 to 48 hours, 2 to 24 hours, 2 to 15 hours, 2 to 9 hours, 2 to 6 hours, 2 to 4 hours, 4 to 72 hours, 4 to 48 hours, 4 to 24 hours, 4 to 15 hours, 4 to 9 hours, 4 to 6 hours, 6 to 72 hours, 6 to 48 hours, 6 to 24 hours, 6 to 15 hours, 6 to 9 hours, 9 to 72 hours, 9 to 48 hours, 9 to 24 hours, 9 to 15 hours. The most preferably, the appropriate time in stirring step is 30 minutes, 1, 2, 4, 6, 9, 15, 24, 48 or 72 hours.

The method of the present invention is carried out at room temperature (20° C. to 25° C.) and under normal atmospheric pressure (about 1013.25 mbar). No control of pressure and/or temperature is needed.

In some embodiments of the method of the present invention, the UV light (ultraviolet light) has a wavelength in the range from 100 to 400 nm, preferably in the range of from 315 to 400 nm. In other embodiments of the method of the present invention, the intensity of the light may be in the range 1 to 150 mW/cm$^2$, such as 10 to 150 mW/cm$^2$, such as 50 to 150 mW/cm$^2$, such as 90 to 150 mW/cm$^2$, such as 130 to 145 mW/cm$^2$. The light intensity may be around 100 mW/cm$^2$.

In the method of the present invention, recovering terephthalic acid from the reaction mixture can be carried out by any suitable method, such as:
  adding water into the reaction mixture until the reaction mixture is clear;
  separating the reaction mixture into a first solid phase and a first liquid phase;
  acidifying the first liquid phase (with for example concentrated HCl) until a terephthalic acid precipitate is formed;
  filtering the terephthalic acid precipitate and washing the terephthalic acid precipitate with water and alcohol (for example EtOH).

In some embodiments, separating the reaction mixture into the first solid phase and the first liquid phase may include filtering the reaction mixture.

In the method of the present invention, recovering ethylene glycol from the reaction mixture can be carried out by any suitable method, such as:
  collecting the dissolved ethylene glyocol in the liquid phase;
  distilling the liquid phase until ethylene glycol is collected.

In some embodiments, the method of the present invention may further include recovering the metal oxide from the reaction mixture. The recovering of the metal oxide from the reaction mixture can be carried out by any suitable method, such as:
  adding water into the reaction mixture until the reaction mixture is clear;
  separating the reaction mixture into a first solid phase and a first liquid phase;
  separating the metal oxide from the first liquid phase (for example by filtration), or separating the metal oxide through washing the terepthalic acid with water and alcohol.

The one or more plastic polymers used in the method of the present invention may be obtained from any suitable source, including without limitation, post-consumer goods, such as beverage bottles, non-beverage containers, food containers, packaging materials, carpeting, clothing, textile fibers, plastic tubes, plastic films, plastic sheets, wrapping materials, and synthetic fibers. In some embodiments, the one of more plastic polymer is not pretreated (no pretreatment and/or no cleaning is required; the plastic polymer as-is is put in contact with the metal oxide in a solution, such as an aqueous alcoholic solution, in the presence of a base and stirred under UV light). In other embodiments, the one or more plastic polymer can undergo a pretreatment, such as cutting, crushing, grinding or pulverizing into flake or other fragments. In other embodiments, it may be necessary to treat the post-consumer goods with one or more of the following processes: pre-washing; coarse-cutting; removal of film and/or paper labels and/or cap material; wet and/or dry grinding; hot wash; caustic wash; rinsing; clean water wash; and flake sorting. The foregoing processes may be used singularly or in combination, in any order, to prepare the plastic polymers for the alkaline hydrolysis and/or depolymerizing reaction.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

The foregoing description will be more fully understood with reference to the following Examples. Such Examples, are, however, exemplary of methods of practising the present invention and are not intended to limit the scope of the invention.

EXAMPLES

Materials and Characterization Methods

Reagents and solvents were purchased from Sigma-Aldrich, TCI, and Carl Roth and used without further purification. Infrared spectra were collected on a Perkin Elmer FT-IR/FIR Frontier Spectrometer from 400 to 4000 cm$^{-1}$. Thermogravimetric analysis (TGA) was performed under air atmosphere on a TA instrument SDT Q600. Dried samples were heated at a rate of 5° C./min until 1000° C. and then cooled to room temperature at a rate of 10° C./min. Powder X-ray diffraction data were collected on a Bruker D8 Advanced using Cu Kα radiation (λ=1.5418 Å, 50 kW/40 mA). $^1$H-$^{13}$C NMR spectra were collected on a 400 MHz Bruker NMR. Elemental analyses (EA) were obtained using a Thermo EA1112 Flash CHNS-O Analyzer.

Experimental Details

General Considerations. All plastics (plastic polymers) used in the experiments were unwashed. PET soda, water bottles, containers were found in the lab office recycling bin, or home recycling bins, and if possible had their lids and labels removed before they were cut into a various assortments of sizes by hand. The clothing, fabrics and microfiber cloths were gently used, and sourced from end consumers.

Chemical Degradation of PET using TiO$_2$. To study the alkaline hydrolysis of PET, the set-up shown in FIG. 1 has been developed. Here, the experiment involves removing the cap and label from a PET bottle, cutting it into random sized pieces and then placing them in the reactor. In a 500 mL Pyrex reactor wrapped with black light UV LEDs (12 W), NaOH (10-60 g), PET (8-30 g), and (10-720 mg) P25 $TiO_2$ are stirred in a 100-400 mL EtOH: $H_2O$ (80:20) solution. Following its completion, $H_2O$ is added until the solution is clear, then filtered. The gold colored liquid is acidified with concentrated HCl until an off white/beige precipitate is formed, and filtered. The reactor was initially allowed to stir at room temperature for 72 hours under UV black light to ensure all PET was depolymerized. The precipitate, TPA, is washed with 300 mL of $H_2O$, 200 mL of EtOH, and dried before being characterized by $^1H$ and $^{13}C$ NMR, IR, TGA and EA.

Figure 2:
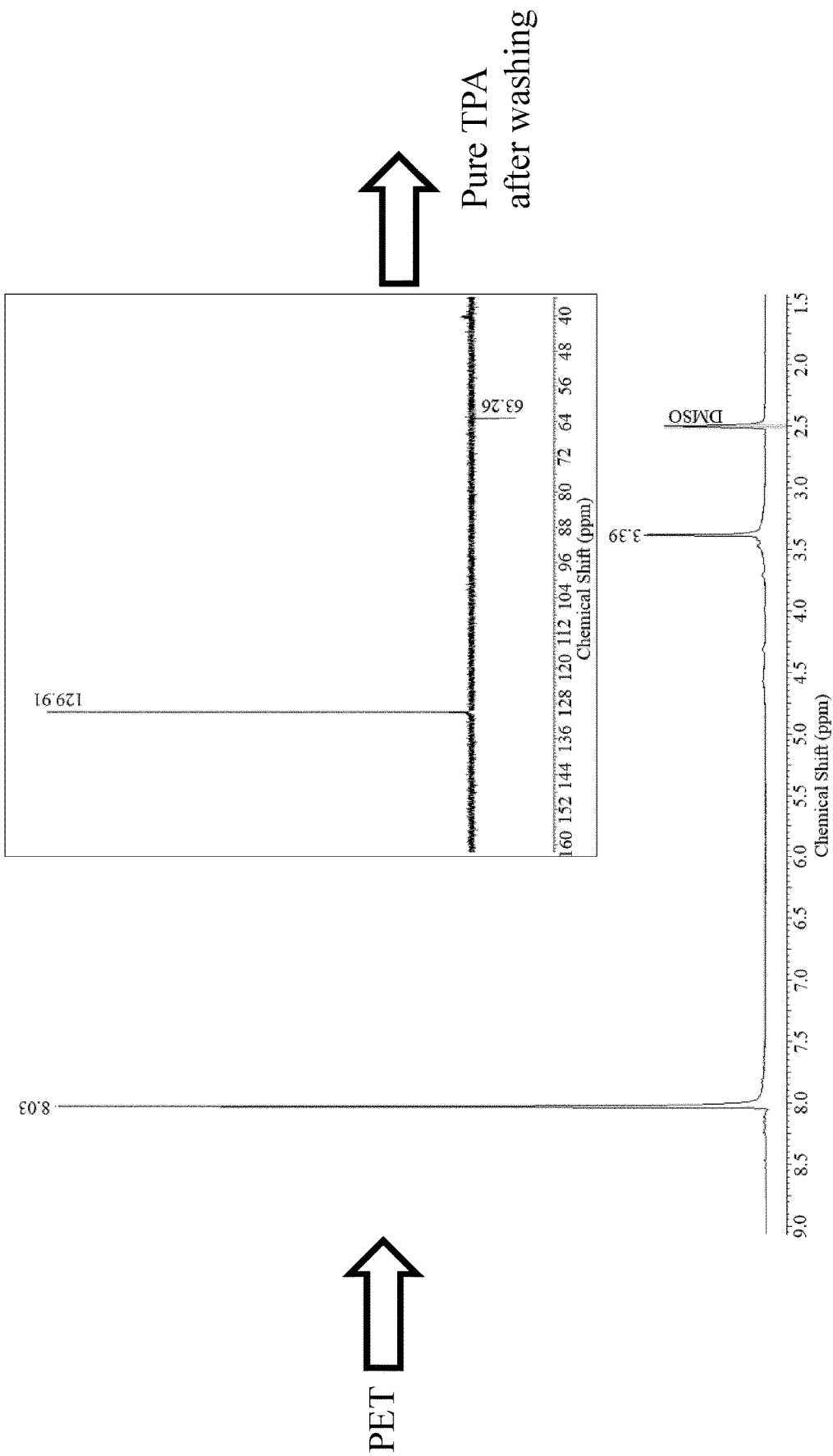
FIG. 2 shows some PET pieces used in the reactor before and after the TPA acquired after (left). $^1$H and $^{13}$C-DEPT135 (inset) NMR of crude TPA obtained prior to washing. Here, both TPA (δ 8.03/129.91) and EG (δ 3.39/63.26) are observed to be products of the reaction.
Figure 3:
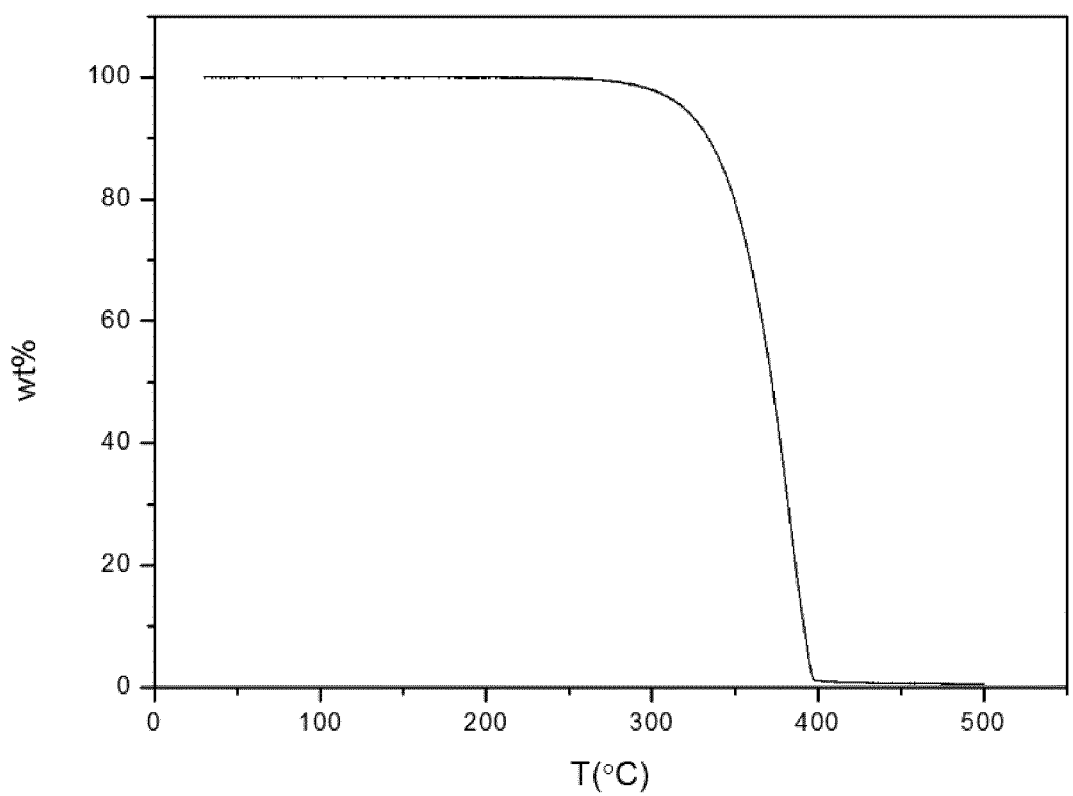
FIG. 3 shows purity of TPA at 9 hours established by TGA shows no presence of NaOH/TiO$_2$ particles, and is in good agreement with the melting point of TPA (300° C.).
Figure 4:
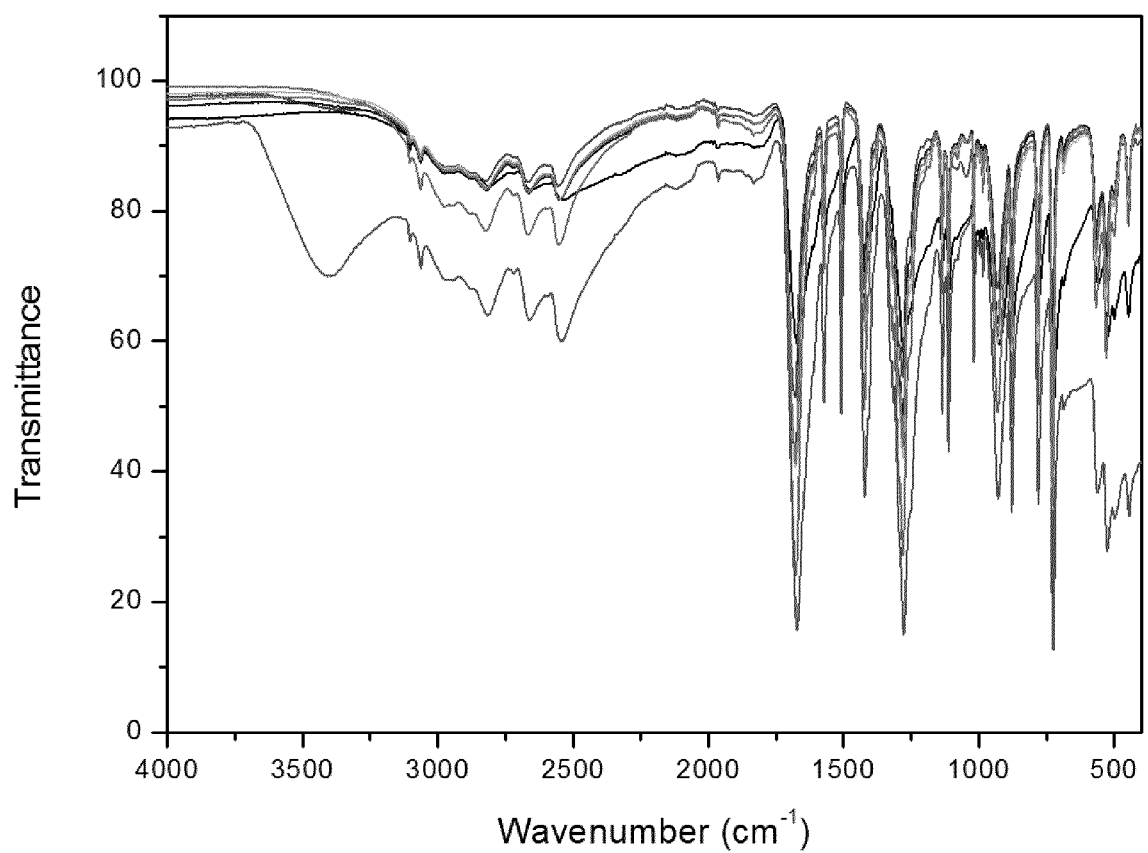
FIG. 4 shows IR of TPA isolated after each reaction. Color scheme: Black, TPA bought from Sigma Aldrich; green, 9 hrs before wash; brown, 9 hrs after wash; red, no TiO$_2$; blue, just NaOH (no UV/TiO$_2$); pink, 1:3 PET:NaOH; bright blue, 1:1 PET:NaOH.

Upon completion, a yield of 89% TPA was afforded which is calculated based off of the average molecular weight of repeating units in PET (192.2 g/mol). Analysis of the crude product by NMR (FIG. 2) shows that both TPA and EG are present in the reaction mixture following work up. Separation of the two products was achieved via washing with water and EtOH. EG was isolated via distillation of the solvent however in a non quantitative yield. To further examine why, blank reactions using just EG and $TiO_2$ in a glass vial were allowed to run for 48 hours, and the crude reaction mixture was analyzed by NMR and gas chromatography (GC) for the presence of $H_2$ and formate. GC analysis shows that the reaction produce 0.2 μmol/g·h of $H_2$, and both $^1H$ and $^{13}C$-DEPT135 NMR show that formate is present at δ(ppm) 8.02 and 170.09, respectively. Therefore, some of the EG in the reaction is being photocatalytically converted to $CO_2$ through a formate intermediate, however the reaction isn't quantitative as EG is still found after the initial reaction before washing, and formate does not appear before washing the crude mixture. Following this, the purity of TPA was confirmed with thermogravimetric analysis (TGA), elemental analysis (EA), infrared (IR), and NMR (FIGS. 3 and 4). The analysis was compared to TPA bought from a commercial source (Sigma Aldrich) and are in good agreement (FIGS. 3 and 4, Table 1).

TABLE 1

Elemental Analysis of TPA from 9-hour reaction using optimized conditions.

| Sample | C % | H % | N % |
|---|---|---|---|
| TPA obtained by the method of the invention | 57.84 | 3.73 | — |
| TPA (Sigma Aldrich) | 57.65 | 3.33 | — |

EA calculated: C: 57.84%, H: 3.64%, O: 38.52%.

Time

Optimization experiment were carried out to analyze the efficiency and limits of this reaction. In particular, it has been investigated to determine the shortest amount of time the reaction could take place in and the optimal ratio of NaOH:PET. Therefore, initial testing began by using the established reaction conditions of 1:7.5 ratio of PET:NaOH, 120 mg $TiO_2$, and 300 mL EtOH:$H_2O$ (80:20).

Figure 5:
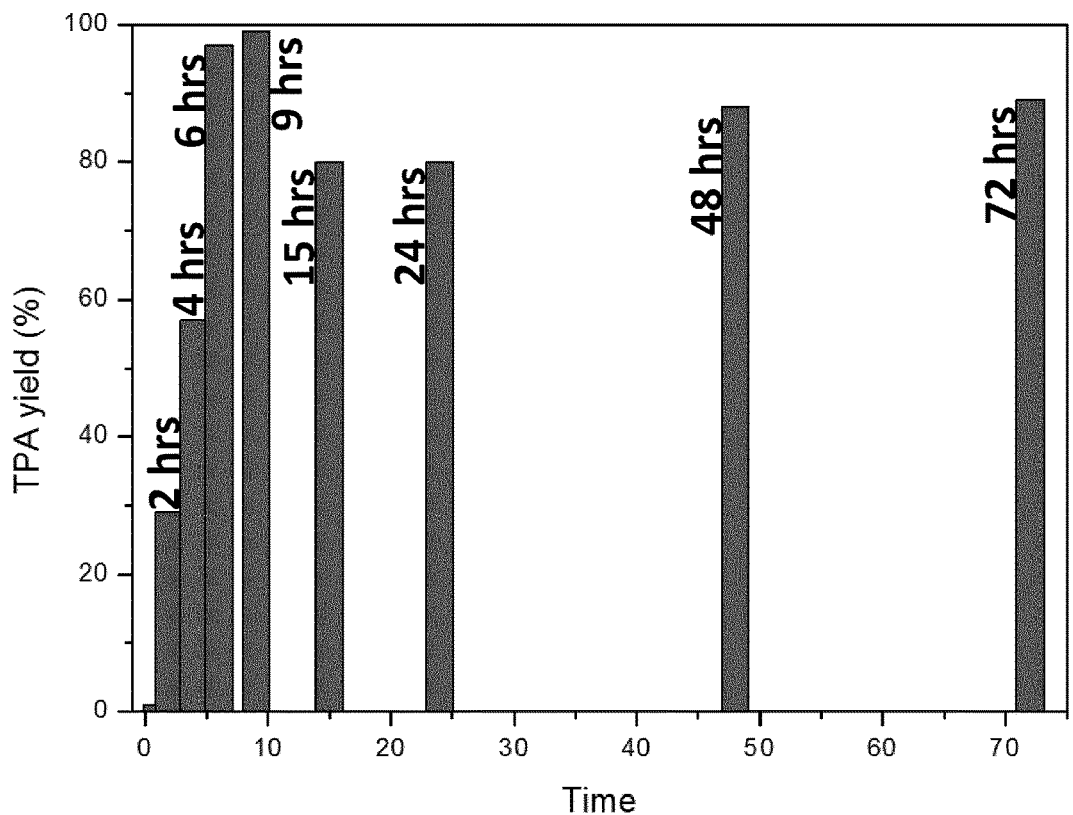
FIG. 5 shows A. Optimization of time for the degradation of PET (cut) in regards to the yield of TPA obtained after the reaction. B. Comparison of reaction times required for cut PET vs powdered PET. C. Optimization of time for PET: NaOH ratio with the quantity of NaOH was kept consistent while the amount of PET used was varied. D. Optimization TiO$_2$ required for room temperature alkaline hydrolysis of PET. Conditions unless otherwise specified were 8 g of PET, 60 g NaOH, 120 mg of TiO$_2$, and 300 mL of a 80:20 EtOH:H$_2$O solution.
Figure 5:
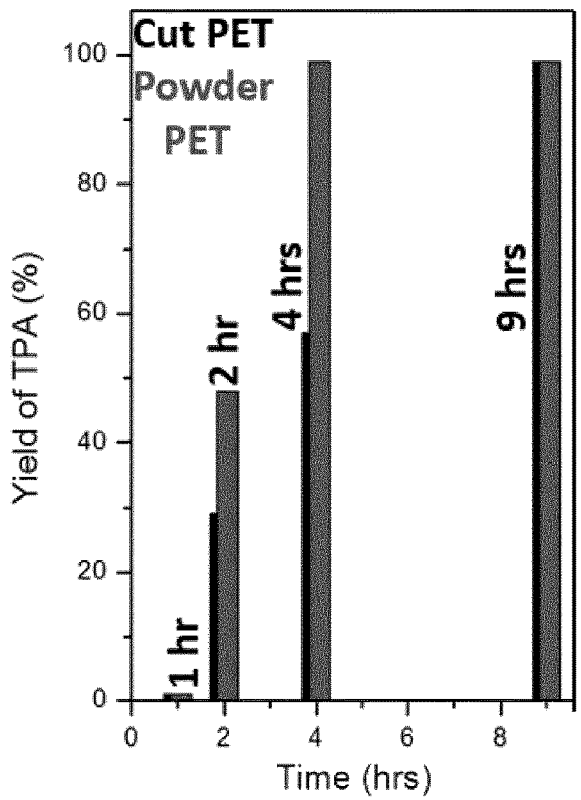
Figure 5:
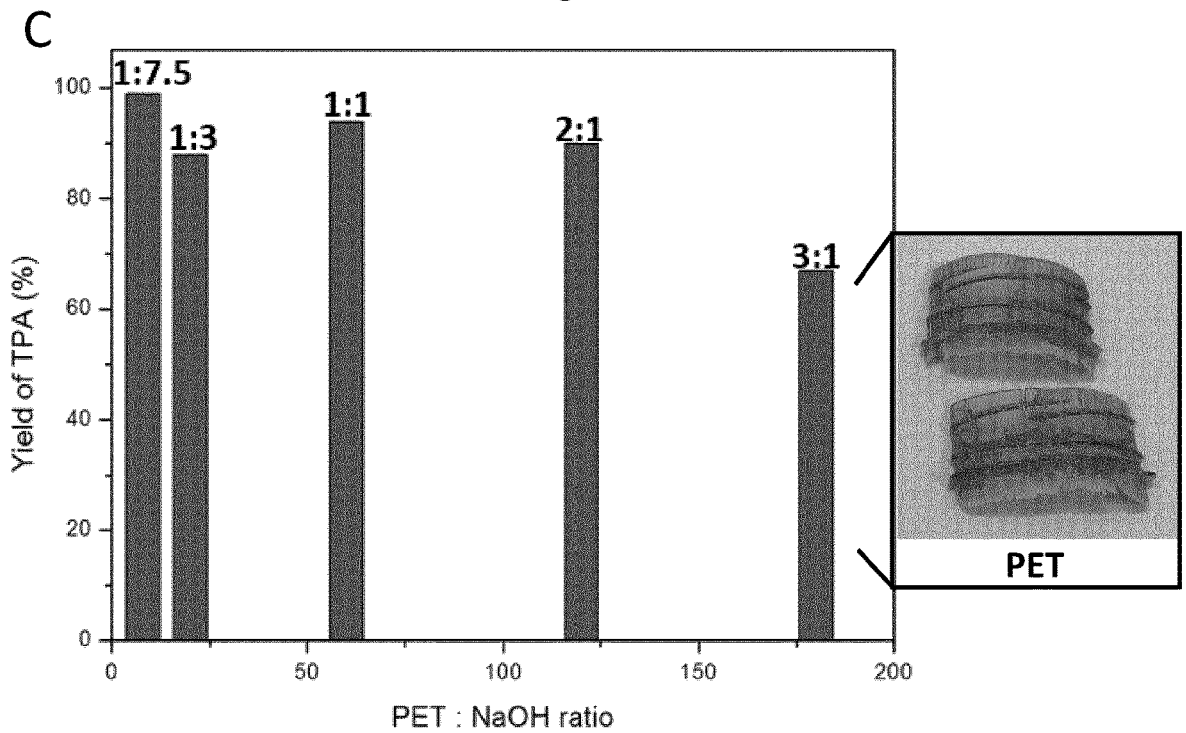
Figure 5:
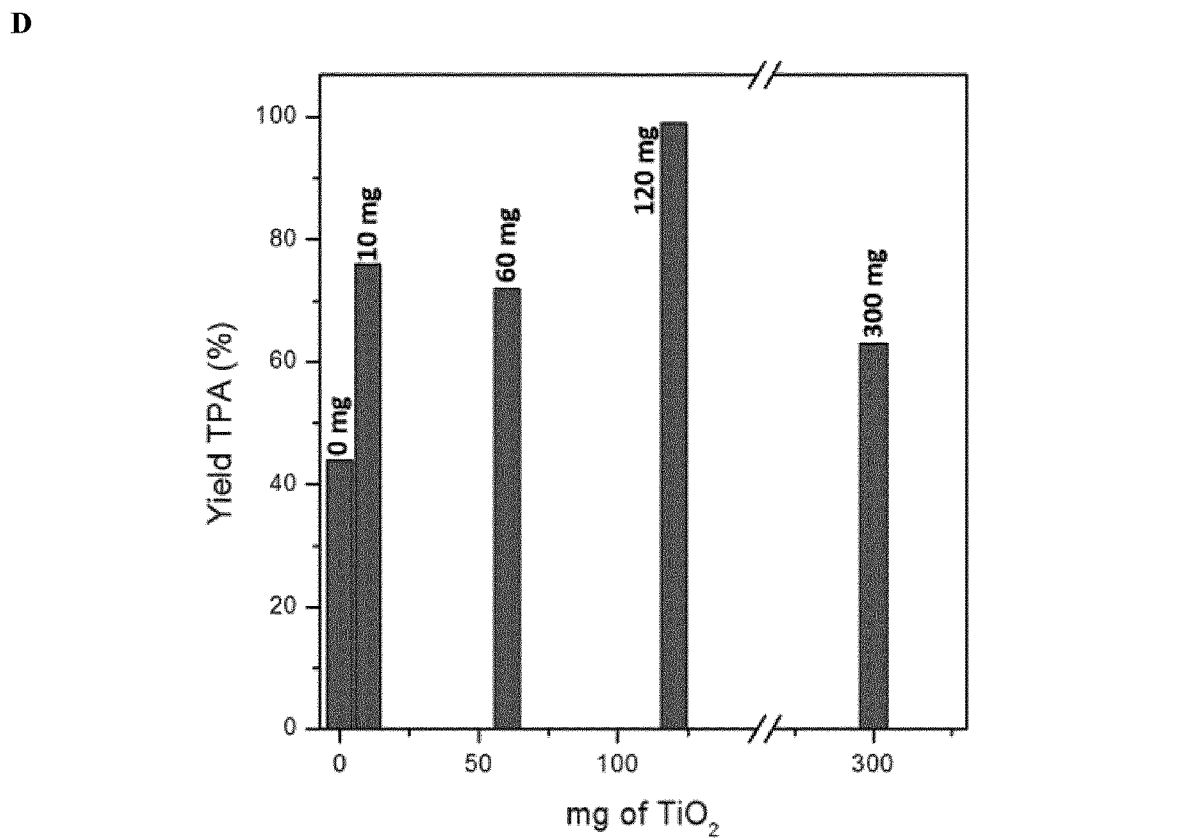

FIG. 5a shows that TPA is produced in the first 4 hours, however the reaction does reach completion and residual PET is recovered. Between 6-9 hours, a rapid increase in yield and maximum conversion of TPA from PET is reached corresponding to a >99% conversion of TPA while a lower conversion rate (89%) is obtained if the reaction continues for 72 hours (Table 2). This drop in yield is assumed to be the photocatalytic degradation of TPA by $TiO_2$ which has been reported for similar conditions. To confirm the conversion of TPA to $H_2$, the reaction was performed in 25 mL glass vials with 10 mL of headspace under UVA irradiation. Reactions were allowed to run for 48 hours, and GC analysis of the headspace showed that 0.5 μmol/g·h of $H_2$ was produced (Table 3).

TABLE 2

Optimization of reaction times using 8 g of PET, 300 mL EtOH:$H_2O$ (80:20), 10% wt NaOH and 120 mg of $TiO_2$. Here, the yield was calculated using an average molecular weight of repeating units in PET (192.2 g/mol) with the mols of TPA obtained.

| Time (hrs) | Yield of TPA (%) |
|---|---|
| 2 | 29 |
| 4 | 57 |
| 6 | 97 |
| 9 | 99 |
| 15 | 80 |
| 24 | 80 |
| 48 | 88 |
| 72 | 89 |

TABLE 3

Gas generated from PET degradation using optimized conditions. Here, reactions were allowed to run for 48 hours. Here, to file PET into a powder, a metal file was used.

| Plastic | $H_2$ (μmol/g · h) |
|---|---|
| PET: Cut | 0.5 |
| PET: Powder | 1.14 |
| Blank: Only TPA | 0.28 |
| Blank: Only EG | 0.20 |

Grinding/Cutting

Increasing the reaction rate was achieved by mechanical filing of the PET plastic into a powder (FIG. 5b, Table 4). Here, the yield increased by ~1.5 times within the first two hours to 48%, with the reaction reaching completion in as little as 4 hours. These results suggest that the increased amount of PET plastic surface area indeed plays a role in the reaction rate. Compared to these results, similar or lower conversions of PET to TPA have been reported at significantly higher temperature to reduce the reaction time. However, the additional energy requirement outweighs the benefit of the results.

TABLE 4

PET degradation due to compositions using optimized reaction conditions. Here, PET was filed with a mechanical metal file into a powder. Here, the yield was calculated using an average molecular weight of repeating units in PET (192.2 g/mol) with the mols of TPA obtained.

| PET Composition | Time (hrs) | Yield of TPA (%) |
|---|---|---|
| Cut | 2 | 29 |
| Cut | 4 | 57 |
| Cut | 48 | 88 |
| Powder | 2 | 48 |
| Powder | 4 | 99 |
| Powder | 48 | 64 |

PET:NaOH Ratio

The ratio of PET:NaOH has been subsequently optimized, as it has been previously stated that the ideal ratio if 1:20. The initial ratio used with the established reaction conditions begins at 1:7.5, which is 8 g:60 g of PET:NaOH (Table 5). To push the boundaries of these conditions, the amount of NaOH was kept the same and varied the quantity of PET while using the same conditions as previously stated. Increasing the quantity of PET to 20 g (1:3), 60 g (1:1) and 120 g (2:1) saw yields of 87%, 95% and 90%, respectively (FIG. 5c). As the ratio is increased, the solution's viscosity increases to the point of almost solidifying, which results in a slight decrease of yield. This is due to the saturation point of TPA in the solution, which leads to the improper mixing of the solution, and the inability of UV light to activate the $TiO_2$ to aide in the depolymerization process. When ratios get too high (3:1 of PET:NaOH) the yield drops considerably to 67%. Here, large amounts of unreacted PET are recovered after the reaction, and in particular the thickest areas (e.g. bottle tops) are found (FIG. 5c, right) with jagged edges along the thinner parts of the tops.

TABLE 5

Optimization of the PET:NaOH ratio used. Here, the amount of NaOH was kept constant (60 g) and the value of PET was changed. Reactor vessel contained 0.120 g of $TiO_2$, 300 mL EtOH:$H_2O$ (80:20), and proceeded for 9 hours. Here, the yield was calculated using an average molecular weight of repeating units in PET (192.2 g/mol) with the mols of TPA obtained.

| Ratio (PET:NaOH) | Yield of TPA (%) |
|---|---|
| 1:0 | 0 |
| 1:7.5 | 99 |
| 1:3 | 88 |
| 1:1 | 94 |
| 2:1 | 90 |
| 3:1 | 67 |
| 1:14 | 76 |

Base

The base has been changed from NaOH to NaO$^t$Bu or KOH, the yield of the reaction either drops significantly, or is similar (Table 6).

TABLE 6

PET degradation using different types of bases. The ratio of the bases was kept to 1:7.5, unless otherwise specified. The reactor vessel contained 0.120 g of $TiO_2$, 300 mL EtOH:$H_2O$ (80:20), and proceeded for 9 hours. Here, the yield was calculated using an average molecular weight of repeating units in PET (192.2 g/mol) with the mols of TPA obtained.

| Base | Yield of TPA (%) |
|---|---|
| NaO$^t$Bu | 36 |
| KOH | 81 |

Metal Oxide and UV Lights

To understand the effect of the $TiO_2$ and UV lights on the depolymerization process of PET, some experiments without UV black lights were carried out and varying concentrations of $TiO_2$. These conditions were used to gain insights on the role of radicals in the reactions. Overall, the hypothetical reaction mechanism is believed to be a combination of the already established alkaline hydrolysis mechanism, with the addition of radical species that are generated by $TiO_2$ from the UV black light. Here, species such as $O^{2-}$, HOO—, HOOH, HOO$^-$, HO—, and OH$^-$ can be produced from $TiO_2$ in a basic aqueous solution. Subsequently, these radicals play a significant role in the depolymerization of PET by increasing the reactions rate.

Figure 6:
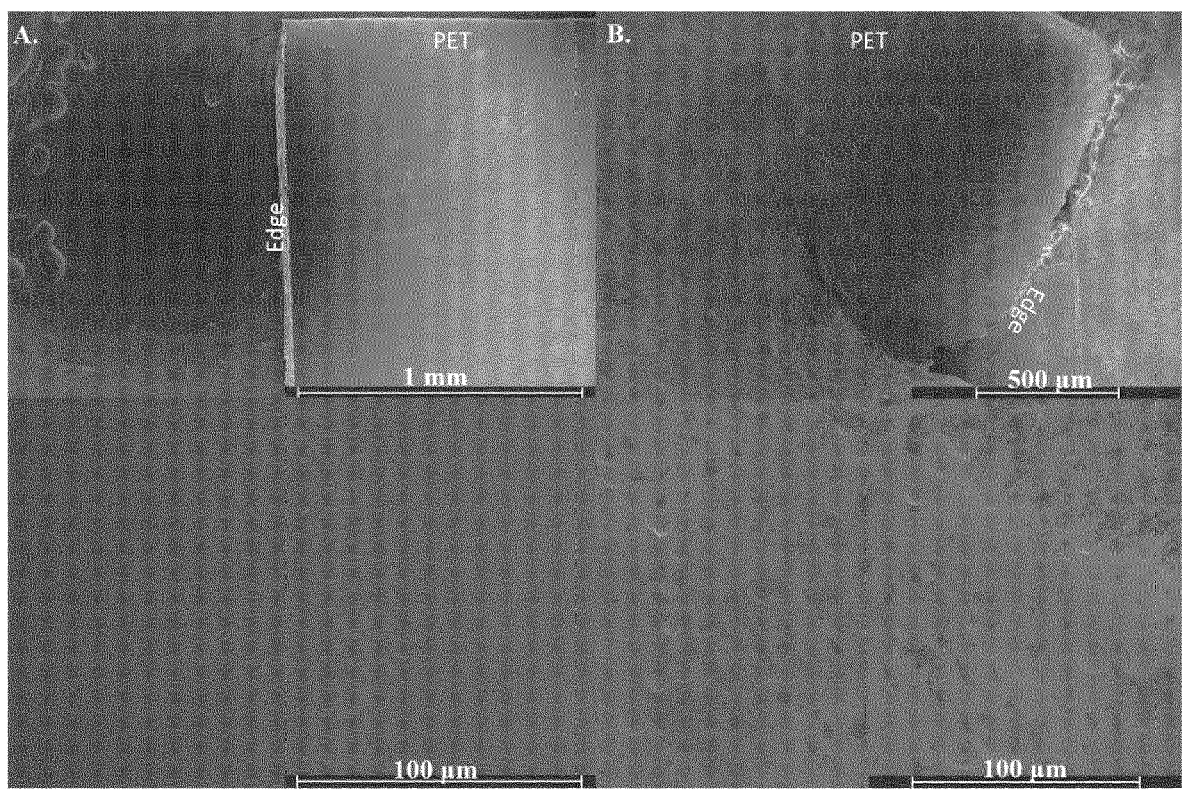
FIG. 6 shows SEM images of PET before (A) and after (B) room temperature hydrolysis using alkaline hydrolysis without TiO$_2$ and UV black lights. Top figures of A and B show the edges of the PET which had been cut (before) or deformed (after), and the overall change in the surface.

Initial experiments were carried out in the absence of $TiO_2$ and UV light to understand the role of NaOH. These experiments were carried out at room temperature using NaOH in a 500 mL glass beaker. Following the addition of PET, the reaction was allowed to stir for 24 hours, and upon filtration 44% of PET is recovered, with the majority of unreacted plastic comprised of the thickest area of the bottles screw top. Scanning electron microscopy (SEM) was used to further examine the residual plastic (FIG. 6), and showed a dramatic change in the surface going from smooth to almost pocked-like. These results highlight that the decomposition of PET using an alkaline solution takes place both on the surface, and edges of the plastic pieces.

Following the confirmation that $TiO_2$ and UV black lights are required to enhance the reactions rate, the quantity of $TiO_2$ required for the reaction was examined using 0-300 mg of $TiO_2$ (Table 7).

TABLE 7

Optimization of amount and type of metal oxide used. Reactor vessel contained 8 g of PET, 300 mL EtOH:$H_2O$ (80:20), 10% wt NaOH, and proceeded for 9 hours. Here, the yield was calculated using an average molecular weight of repeating units in PET (192.2 g/mol) with the mols of TPA obtained.

| Metal Oxide | Amount (g) | Yield of TPA (%) |
|---|---|---|
| $TiO_2$ | 0.300 | 63 |
| $TiO_2$ | 0.120 | 99 |
| $TiO_2$ | 0.060 | 72 |
| $TiO_2$ | 0.010 | 76 |
| — | 0 mg (blank) | 44 |

As can be seen in FIG. 5d, TPA is obtained for all reactions, with the lowest yield of 44% attributed to the absence of $TiO_2$. Here, the yield is consistent with those found for the absence of both $TiO_2$ and UV black light, demonstrating that the addition of only UV light into the reaction does not lead to an increased yield. As the amount of $TiO_2$ is increased, the change in yield is initially dramatic and then stabilizes, with the highest yield associated with 120 mg (>99%). Increasing the amount of $TiO_2$ to 300 mg leads to a significantly lower yield of 63% which is attributed to the photocatalytic degradation of TPA by $TiO_2$.

Figure 7:
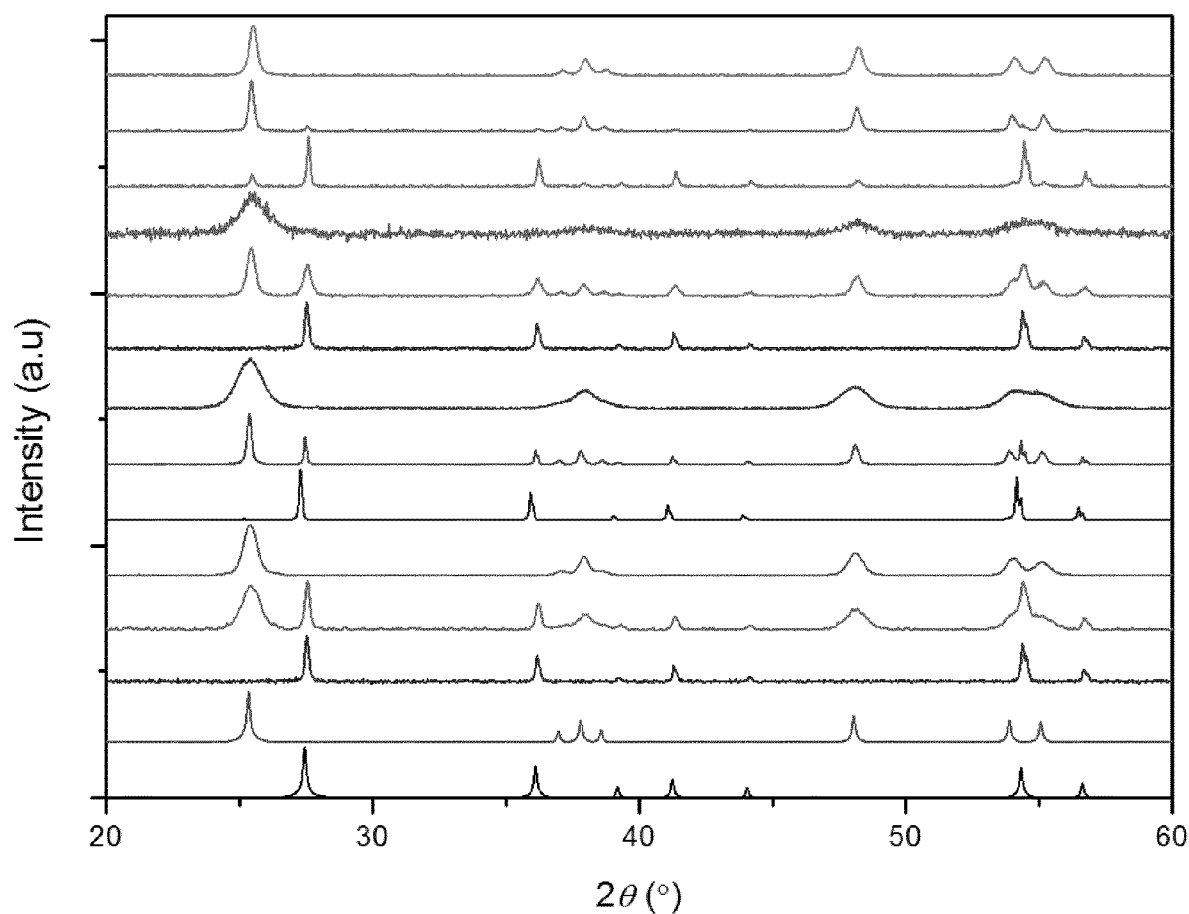
FIG. 7 shows PXRD of TiO$_2$ phases obtained through different synthetic methods. Here, R=rutile, A=anatase and R/A=a mix of rutile and anaphase. Color scheme: black, R (theory); red, A (theory); blue, hydrothermal R; pink, hydrothermal R/A; green, hydrothermal A; dark blue, solgel R; purple, solgel R/A; dark purple, solgel A; burgundy, MOF derived R; mustard yellow, MOF derived R/A; sky blue; MOF derived A; seaform green, precipitate R; brown, precipitate R/A; bright green, precipitate A.

To analyze the role of $TiO_2$ in the reaction, different types of $TiO_2$ were sourced and synthesized to determine if the particle size, anatase:rutile ratio, the degree of anatase/rutile interaction and the band gap play a role in the mechanism (Table 8, FIG. 7). Composites were also prepared to understand if the electron hole separation could be optimized. In all cases, the anatase form of the $TiO_2$ composites underperformed compared to the mixed or rutile phase. This is due to the better electron/hole separation and efficiency found in the anatase and rutile mixtures, as well as the smaller band gap (3.0 vs 3.2 eV for anatase) found in rutile. Therefore, the rutile phase absorbs more light in the UVA region than anatase and subsequently increasing the amount of radicals in the reaction, affording higher yields.

TABLE 8

Radical degradation of PET using different compositions of TiO₂ either prepared or bought. References found beside the entries phase are the literature method used for its preparation. If no reference is found please see the supporting information for more details. Reactions conditions used were 1:7.5 PET (powder):NaOH ratio, 300 mL of a 80:20 EtOH:H₂O solution, using UV black lights, 120 mg of TiO₂ phase(s) and a reaction time of 4 hrs using powdered PET.

| Entry | TiO₂ Preparation Method and Phase | Yield of TPA (%) |
| --- | --- | --- |
| 1. | MOF derived: anatase (100%)[1] | 51 |
| 2. | MOF derived: anatase:rutile (70:30)[1] | 68 |
| 3. | MOF derived: rutile (100%)[1] | 74 |
| 4. | Sol-gel: anatase (100%) | 81 |
| 5. | Sol-gel: anatase:rutile (70:30) | 89 |
| 6. | Sol-gel: rutile (100%) | 82 |
| 7. | Precipitation: anatase (100%) | 57 |
| 8. | Precipitation: anatase:rutile (70:30) | 84 |
| 9. | Precipitation: rutile (100%) | 92 |
| 10. | Commercial anatase (100%) | 89 |
| 11. | Commercial rutile (100%) | 94 |
| 12. | Hydrothermal: anatase (100%) | 61 |
| 13. | Hydrothermal: anatase:rutile (70:30) | 90 |
| 14. | Hydrothermal: rutile (100%) | 67 |
| 15. | Commercial: P25 | 99 |
| 16. | Pt-P25 (TiO₂) | 49 |
| 17. | Pd-P25 (TiO₂) | 73 |
| 18. | Ru-P25 (TiO₂) | 98 |
| 19. | RuO₂-P25 (TiO₂) | 71 |
| 20. | ZnO$_x$-P25* (TiO₂) | 93 |
| 21. | ZnO-P25 (TiO₂) | 87 |

*Reduced ZnO on P25 with unknown oxidation state.

The addition of another metal onto the P25 (TiO₂) surface such as Pt, Zn, Ru and Pd gave interesting results, with Pt, Pd, and RuO₂-P25 (TiO₂) underperforming the commercial P25 and Ru-P25 due to their reduction ability (Table 9). While no PET was left over in the reaction, the lower yields of TPA are attributed to their ability to photocatalyse competing back reactions, which degrade TPA into gases such as H₂. Although Ru is a platinum group metal, it isn't commonly used as a co-catalyst in reduction reactions, and so the effect of the back reactions in minimal, rendering yields similar to P25 (TiO₂). Further confirming the role of TiO₂, ZnO was substituted into the reaction and the yield was observed to decrease to 62%. Both semiconductor metal oxides have been reported to have similar photocatalytic behavior, however ZnO has a slightly larger band gap (3.4 vs. 3.0 ev). Whilst this could be a factor, the difference in yields could be due to the fact that the TiO₂ used for this reaction is P25, which is a mixture of anatase and rutile, and is known for providing excellent electron/hole separation, and overall efficiency. These results solidify the fact that UV black light activated TiO₂ is required for the reaction.

TABLE 9

Optimization of amount and type of metal oxide used. Reactor vessel contained 8 g of PET, 300 mL EtOH:H₂O (80:20), 10% wt NaOH, and proceeded for 9 hours. Here, the yield was calculated using an average molecular weight of repeating units in PET (192.2 g/mol) with the mols of TPA obtained.

| Metal Oxide | Yield of TPA (%) |
| --- | --- |
| ZnO | 63 |
| ZrO₂ | 85 |
| Nb₂O₅ | 75 |
| Ta₂O₅ | 82 |

TABLE 9-continued

Optimization of amount and type of metal oxide used. Reactor vessel contained 8 g of PET, 300 mL EtOH:H₂O (80:20), 10% wt NaOH, and proceeded for 9 hours. Here, the yield was calculated using an average molecular weight of repeating units in PET (192.2 g/mol) with the mols of TPA obtained.

| Metal Oxide | Yield of TPA (%) |
| --- | --- |
| RuO | 68 |
| Fe₂O₃ | 70 |
| WO | 72 |

Subsequently, since TiO₂ is required for the depolymerization of PET via radicals, a radical scavenger was introduced into the reaction. Here, (2,2,6,6-Tetramethylpiperidin-1-yl)oxyl (TEMPO) was used in a 2:1 ratio of TEMPO:TiO₂ (120 mg), using the same optimized conditions. The depolymerization reaction was suppressed, and a yield of only 55% TPA was recovered after 9 hours, confirming the role of radicals within the alkaline hydrolysis mechanism. However further studies are needed to identify which radical(s) are present, and how they influence the kinetics in the depolymerization process. In the absence of UV light or TiO₂, or in the event the solution becomes too viscous, the yields of TPA decrease substantially. If the concentration of radicals within the solution becomes too abundant, a competing and/or side reaction mechanism such as the photocatalytic degradation of TPA, begins to occur.

Coloured PET and/or Contaminated PET Plastic Materials

The reaction conditions can be extended to demonstrate its applicability for recycling different colored PET bottles (Table 10, Table 11, Table 12). The conditions used were 400 mg of plastic, 3 g NaOH, 300-400 mL of a 80:20 EtOH:H₂O solution, using UV black lights, and 100-140 mg of TiO₂ as the catalyst, unless otherwise specified. The reaction time was 9 hours with cut PET to demonstrate that contaminates do not interfere with the process. Experiments show that colored PET bottles (green, brown, black, and white) behaved as expected, however gave lower yields of 72%, 67%, 27%, and 78% respectively, due to the presence of additives. A 1:1:1:1:1 mixture of green:brown:black:white:clear plastics was tested and afforded a 97% yield of pure TPA, demonstrating that the presence of different additives/dyes does not affect the reactions ability to depolymerize PET.

Many of the literature studies present on the depolymerization of PET use pre-washed or chemical grade PET pellets. However, application of their set up into a real industrial scenario does not take into account issues like unwashed or dirty PET that is obtained from a regular households garbage. Here, discarded materials can contain compounds such as surfactants, lotions, proteins, sugars, food particles etc. which may change the way in which their system behaves. To demonstrate that our conditions are applicable to a wide range of consumer products, pieces of dirty cut PET were reacted for 9 hours (Table 10). Cut PET plastic pieces were chosen instead of powdered to ensure that the contaminates remained intact and were not removed by mechanical filing. Unsurprisingly, soda bottles had the highest yield amount other contaminated samples such as peanut butter, face lotion and milk shake bottles. This is likely due to the interaction of the radicals produced by TiO₂ with other organic compounds instead of the plastic. To combat this, the amount of TiO₂ was tripled (360 mg) and found that the yield increased.

Different Plastic Material

Further exploring depolymerization of ester based polymers, the susceptibility of both polybutylene terephthalate (PBT) and poly-lactic acid (PLA) was examined to the conditions of the method of the present invention. In both cases, no polymer was found following the completion of the reaction; however yields were lower than expected. This could be due to the further decomposition of the monomers by $TiO_2$ to $H_2$, however further studies are need to confirm this and subsequently optimize the conditions.

TABLE 10

Degradation of various PET plastics using conditions stated above. The reaction time was 9 hours with cut PET to demonstrate that contaminates do not interfere with the process. Here, the yield was calculated using an average molecular weight of repeating units in PET (192.2 g/mol) or other plastic with the mols of TPA or other monomer obtained.

| Plastic | Contaminant | Source, color | Time (hrs) | Yield of TPA (%) |
|---|---|---|---|---|
| PET | None | Ice Tea bottle: brown | 4 | 67 |
| PET | None | Waterbottle: green | 4 | 72 |
| PET | None | Food container: black | 4 | 27 |
| PET | None | Milkshake bottle: white | 4 | 78 |
| PET | None | Brown:Green:Black:Clear:White (1:1:1:1:1) | 4 | 97 |
| PET | Sugar/syrup | Soda bottle/Water bottle, clear | 9 | >99 |
| PET | Face lotion | Clinique Face Lotion, clear | 9 | 50/82* |
| PET | Peanut butter | Crunchy, Store Brand, clear | 9 | 85 |
| PET | Ketchup | Heinz Ketchup Bottle, Red | 9 | 38* |
| PET | Soap | Hand soap, clear | 9 | 85* |
| PET | Milkshake | High protein milkshake, white PET bottle | 9 | 60/80* |
| PET | Shampoo Crème | Surfactants, hair cream, Beige/Gold PET bottle | 9 | 63* |
| PBT (Polybutylene terephthalate) | — | Sigma Aldrich | 9 | 62 (TPA) |
| PLA (Poly-lactic acid) | — | Sigma Aldrich | 9 | 43 |
| Microfiber cloth: 80% polyester 20% polyamide | — | Blue cloth | 9 | 67% (TPA) |
| Cotton Polyester Blend (35% cotton, shirt) | — | White dress shirt | 9 | 92% (TPA) |

*represent yield with 360 mg of $TiO_2$ used.

While post-consumer PET waste is commonly associated with plastic bottles and food containers, clothing and fabrics also fall into this category. Therefore, selective depolyermization of polyester based fabrics was also tested. Here, both the polyester/polyamide microfiber cloths (67% TPA) and cotton blend shirt (92% TPA) were successfully depolymerized and left behind the residual polyamide and cotton components. The residual polymers and fabrics can subsequently be recycled back to their starting components, or reused.

TABLE 11

Degradation of various dirty PET plastics using the conditions stated above unless otherwise specified. The reaction time was 9 hours with cut PET to demonstrate that contaminates do not interfere with the process. Here, the yield was calculated using an average molecular weight of repeating units in PET (192.2 g/mol) with the mols of TPA obtained.

| Contaminant | Source, color | Yield of TPA (%) |
|---|---|---|
| Sugar/syrup | Soda bottle (various) | >99 |
| Face lotion | Clinique Face Lotion, clear PET | 50/82* |
| Peanut butter | Crunchy, Store Brand, clear PET container | 85 |
| Ketchup | Heinz Ketchup Bottle, Red PET container | 38* |
| Soap | Surfactant(s) | 95* |
| Milkshake | High protein milkshake, white PET bottle | 60/80* |
| Shampoo Crème | Surfactants, hair cream, Beige/Gold PET bottle | 63* |

*represent yield with 360 mg of $TiO_2$ used.

Depolymerization of Mixed Plastics, Clothing and Fibers

Further exploring depolymerization of ester based polymers, the susceptibility of both polybutylene terephthalate (PBT) and poly-lactic acid (PLA) was examined to the conditions of the method of the present invention. In both cases, no polymer was found following the completion of the reaction; however yields were lower than expected. This could be due to the further decomposition of the monomers by $TiO_2$ to $H_2$, however further studies are need to confirm this and subsequently optimize the conditions.

While post-consumer PET waste is commonly associated with plastic bottles and food containers, clothing and fabrics also fall into this category. Therefore, selective depolymerization of polyester based fabrics was also tested. Here, both the polyester/polyamide microfiber cloths (67% TPA) and cotton blend shirt (92% TPA) were successfully depolymerized and left behind the residual polyamide and cotton components.

The residual polymers and fabrics can subsequently be recycled back to their starting components, or reused.

TABLE 12

Degradation of mixed plastics and polyethylene blended fabrics, using the conditions sated above unless otherwise specified. Here, the yield was calculated based on the average molecular weight of repeating units in PET (192.2 g/mol) or other plastics with the mols of TPA or other monomer(s) obtained.

| Plastic | Monomer(s) | Time (hrs) | Yield (%) |
| --- | --- | --- | --- |
| PET: Brown | TPA/EG | 4 | 67 |
| PET: Green | TPA/EG | 4 | 72 |
| PET: Black | TPA/EG | 4 | 27 |
| PET: White | TPA/EG | 4 | 78 |
| PET: Brown:Green:Black:Clear:White (1:1:1:1:1) | TPA/EG | 4 | 97 |
| PBT (Polybutylene terephthalate) | TPA/1,4-butanol | 9 | 62 (TPA) |
| Poly-lactic acid (PLA) | Lactic acid | 9 | 43 |
| Microfiber cloth: 80% polyester 20% polyamide | TPA/Caprolactam or α,ω-amino acids or diamine and a diacid | 9 | 67% TPA |
| Cotton Polyester Blend (35% cotton, shirt) | TPA | 9 | 92% TPA |
| Stretch Pants (15% polyester, 2% Spandex, 83% Cotton) | TPA | 9 | 80% TPA |
| PET: Clear bottle PVC/PVDC:Orange blister package Paper Towel:brown (8:1:1:1:1) | TPA | 9 | 71% TPA |

Depolymerization of PET Conditions

1. Following the same procedure outlined above, the reaction was left to run for 1 month. Result: TPA yield: 89%.

2. Following the same procedure outlined above, with the modification of the amount of $TiO_2$ added as seen in Table 13. The reaction time can be lowered to 30 min. using 720 mg of $TiO_2$.

TABLE 13

Reaction length and TPA yield with increasing amounts of $TiO_2$.

| Amount (mg) | Time (hrs) | Yield (TPA) |
| --- | --- | --- |
| 120 | 3 | 87 |
| 360 | 3 | 97 |
| 480 | 2 | 90 |
| 620 | 2 | 90 |
| 660 | 1.5 | 81 |
| 660 | 1 | 93 |
| 660 | 30 min | 75 |
| 720 | 30 min | 86 |
| 720 | 1 | 88 |

$TiO_2$ Sol-Gel Synthesis

The synthesis of the $TiO_2$ sol-get was performed using methods adapted from the literature. Sol-gel was then spread across a glass microscope slide, and placed in a furnace for 2 hrs at 500-650° C., and subsequently allowed to cool to room temperature. The slide was then washed with water and ethanol to remove any excess $TiO_2$. The $TiO_2$-glass slide was then placed inside of a UVA light reactor, along with 8 g of PET plastic, 60 g of NaOH, and 300 mL of a EtOH:$H_2$O (80:20) solution. The reaction was allowed to run for 8 hrs, and was subsequently worked up with the same procedure described earlier.

For multiple coats, the sol-gel was applied to the glass jar, which was then heated in the furnace, and another coat was applied before subsequent heating. The washing step was only performed following the cooling of the final coat.

As can be seen in Table 14, the yields of TPA are comparable to those obtained from sol-gel synthesized $TiO_2$. For each run, the $TiO_2$-glass slides were washed with water and ethanol, and placed back into the reactor. After 4 runs, a drop in yield was observed, and the $TiO_2$-glass was regenerated in a 500° C. oven for 2 hrs. Following regeneration, an increase in yield was observed demonstrating the $TiO_2$ was once again active. Interestingly, a moderate yield of TPA was also observed when just the glass slide was used.

TABLE 14

Yields of TPA using $TiO_2$-glass slides.

| Run # | Yield (TPA) |
| --- | --- |
| 1 | 87 |
| 2 | 81 |
| 3 | 86 |
| 4 | 63 |
| 5 (regen) | 75 |
| Regular glass: No $TiO_2$ | 62 |

Following the same procedure as the sol-gel $TiO_2$ glass, sol-gel $TiO_2$ was coated once on the inside of a 25 mL Duran glass jar, placed in a 500-650° C. furnace, and after cooling and washing the depolymerization reaction was allowed to proceed. Here, the reaction followed the typical PET depolymerizaion conditions, however no additional $TiO_2$ was added. A drop in TPA yield was noted in the second run, and following regeneration of the $TiO_2$-glass jar an increase in yield was observed. Following this, after each run the $TiO_2$-glass jar was regenerated to keep the yield of TPA high (Table 15). If two coats of $TiO_2$ sol-gel were used, the reaction time could be lowered to 3 hrs (Table 16), and if 4 were used, the reaction time could be lowered to 2 hrs (TPA yield 80%).

TABLE 15

TiO$_2$ on 25 mL Duran glass jar (1 coat) Reaction time 4 hrs

| Run # | Yield (TPA) |
|---|---|
| 1 | 81 |
| 2 | 63 |
| 3 | 71 |
| 4 (regen) | 80 |
| 5 (regen) | 83 |
| 6 (regen) | 70 |
| 7 (regen) | 75 |

TABLE 16

TiO$_2$ on 25 mL Duran glass jar (2 coat) Reaction time 3 hrs

| Run | Yield (TPA) |
|---|---|
| 1 | 81 |
| 2 | 64 |
| 3 (regen) | 74 |

Different Reaction Conditions

Further reaction optimization shows that we can perform the reaction in the presence of only EtOH (no water).

TABLE 17

Reaction conditions using new ratios of PET:NaOH, solvent system, and quantity of TiO$_2$.

| Entry | Solvent (type) | Solvent (mL) | PET amount (g) | NaOH amount (g) | TPA (yield) |
|---|---|---|---|---|---|
| 1 | EtOH:H$_2$O | 250:50 | 8 | 60 | >99 |
| 2 | EtOH | 300 | 10.98 | 30 | 70 |
| 3 | EtOH | 150 | 11 | 30 | 80 |
| 4 | EtOH | 150 | 10 | 30 | 90 |
| 5 | EtOH | 125 | 8 | 30 | 90 |
| 6 | EtOH | 100 | 8 | 30 | 87 |
| 7 | EtOH | 75 | 10 | 30 | 87 |
| 8 | EtOH | 110 | 10 | 30 | 77 |

The invention claimed is:

1. A method of alkaline hydrolysis of a polyester into monomers that form the polyester, the monomers comprising terephthalic acid, the method comprising:
   a) contacting the polyester with TiO$_2$ particles in a solution in the presence of NaOH to provide a reaction mixture, the TiO$_2$ particles being added to the solution separately from the polyester, the solution comprising a solvent consisting of (i) alcohol or (ii) a mixture of alcohol and <50 volume % water, the alcohol is selected from the group consisting of methanol, ethanol, propanol, butanol, pentanol, and a combination thereof, a weight ratio of the polyester to the NaOH (polyester:NaOH) is 1:10 to 1:1, and a weight ratio of the polyester to the TiO$_2$ (polyester:TiO$_2$) is 1:0.0375 to 1:0.00125;
   b) stirring the reaction mixture under UV light at room temperature and normal atmospheric pressure for greater than or equal to 6 hours and less than or equal to 9 hours to hydrolyze the polyester into the terephthalic acid, wherein the UV light comprises UVA light having a wavelength in a range of from 315 nanometers to 400 nanometers; and
   c) recovering the terephthalic acid from the reaction mixture, wherein the terephthalic acid recovered from the reaction mixture comprises greater than or equal to 90% of the terephthalic acid from the polyester calculated based on the average molecular weight of repeating units in the polyester.

2. The method of claim 1, wherein the polyester is selected from the group consisting of polyethylene terephthalate (PET), polybutylene terephthalate (PBT), polytrimethylene terephthalate (PTT), polyethylene isosorbide terephthalate (PEIT), and a combination thereof.

3. The method of claim 1, wherein the polyester is polyethylene terephthalate (PET).

4. The method of claim 1, wherein the solvent consists of ethanol.

5. The method of claim 1, wherein the UVA light has an intensity in the range of 1 milliwatt per square centimeter to 150 milliwatts per square centimeter.

6. The method of claim 1, wherein the TiO$_2$ particles comprise rutile TiO$_2$, anatase TiO$_2$, or a combination thereof.

7. The method of claim 1, wherein the solvent consists of the alcohol and the water, and wherein a ratio by volume of the alcohol to the water (alcohol:water) is 80:20 to 90:10.

8. The method of claim 7, wherein the alcohol consists of ethanol.

9. The method of claim 1, wherein the solvent consists of ethanol and water, and wherein a ratio by volume of the ethanol to the water (ethanol:water) is 80:20.

* * * * *